(12) United States Patent  
Shiraki et al.

(10) Patent No.: US 9,089,841 B2  
(45) Date of Patent: Jul. 28, 2015

(54) METHOD OF SAMPLING SPECIMEN, TEST METHOD AND DROPPING PIPETTE AND SPECIMEN SAMPLER TO BE USED THEREIN

(71) Applicant: ARKRAY, Inc., Kyoto-shi, Kyoto (JP)

(72) Inventors: Yasunori Shiraki, Kyoto (JP); Daisuke Matsumoto, Kyoto (JP)

(73) Assignee: ARKRAY, Inc., Kyoto-shi (JP)

( * ) Notice: Subject to any disclaimer, the term of this patent is extended or adjusted under 35 U.S.C. 154(b) by 0 days.

(21) Appl. No.: 13/657,443

(22) Filed: Oct. 22, 2012

(65) Prior Publication Data

US 2013/0055829 A1 Mar. 7, 2013

Related U.S. Application Data

(60) Continuation of application No. 13/359,841, filed on Jan. 27, 2012, which is a division of application No. 12/224,753, filed as application No. PCT/JP2007/054650 on Mar. 9, 2007, now abandoned.

(30) Foreign Application Priority Data

Mar. 9, 2006 (JP) .................. 2006-064030

(51) Int. Cl.
*B01L 3/02* (2006.01)
*B01L 3/00* (2006.01)
*G01N 35/10* (2006.01)

(52) U.S. Cl.
CPC ............. *B01L 3/0272* (2013.01); *B01L 3/0282* (2013.01); *B01L 3/50825* (2013.01); *B01L 3/5635* (2013.01); *B01L 2200/026* (2013.01); *B01L 2400/0481* (2013.01); *G01N 35/1079* (2013.01)

(58) Field of Classification Search
CPC ............. B01L 3/0272; B01L 2200/026; B01L 3/5635; B01L 3/50825; B01L 3/0282; B01L 2400/0481; G01N 35/1079
See application file for complete search history.

(56) References Cited

U.S. PATENT DOCUMENTS 2,957,609 A * 10/1960 Holmes .................... 222/212
3,206,073 A * 9/1965 Scislowicz ................ 222/80

(Continued)

FOREIGN PATENT DOCUMENTS

EP 0126390 A2 11/1984
GB 1541914 A 3/1979

(Continued)

*Primary Examiner* — Jill Warden
*Assistant Examiner* — Julie Tavares
(74) *Attorney, Agent, or Firm* — Fox Rothschild LLP

(57) ABSTRACT

A method for taking a sample includes drawing blood into a vacuum blood collection tube and transferring at least part of the blood from the vacuum blood collection tube to a sample storage space of a dropper. The vacuum blood collection tube includes a sample storage portion and a stopper sealing the sample storage portion, and the drawing is performed by stabbing a hollow needle into the stopper. The dropper includes and internal space at least part of which is the sample storage space for storing a sample and which includes a volume changeable space defined, by an elastically deformable portion having flexibility. The dropper further includes an insertion portion including a through-hole connected to the internal space, and the transfer of the sample is performed by inserting the insertion portion into a through- formed in the stopper by the stabbing of the hollow needle into the stopper.

14 Claims, 16 Drawing Sheets

(56) References Cited

U.S. PATENT DOCUMENTS

| | | | |
|---|---|---|---|
| 3,608,550 A * | 9/1971 | Stawski | 604/414 |
| 4,250,893 A | 2/1981 | White | |
| 4,808,381 A * | 2/1989 | McGregor et al. | 422/512 |
| 4,871,355 A | 10/1989 | Kikkawa | |
| 5,135,489 A | 8/1992 | Jepson et al. | |
| 5,163,583 A | 11/1992 | Whitworth | |
| 5,169,602 A | 12/1992 | Pang et al. | |
| 5,344,666 A | 9/1994 | Levine | |
| 5,397,026 A | 3/1995 | Mayes | |
| 5,697,522 A | 12/1997 | Mayes | |
| 5,801,062 A | 9/1998 | Sarstedt et al. | |
| 6,312,648 B1 | 11/2001 | Lenardo et al. | |
| 2001/0048898 A1 | 12/2001 | Buehler | |
| 2008/0125673 A1 * | 5/2008 | Carano et al. | 600/584 |

FOREIGN PATENT DOCUMENTS

| | | |
|---|---|---|
| JP | 04-259452 A | 9/1992 |
| JP | 05-228379 A | 9/1993 |
| JP | 09-079953 A | 3/1997 |
| JP | 10-179555 A | 7/1998 |
| JP | 11-101795 A | 4/1999 |
| JP | 2005-244366 A | 9/2005 |
| WO | 99/45360 A1 | 9/1999 |

* cited by examiner

PRIOR ART

METHOD OF SAMPLING SPECIMEN, TEST METHOD AND DROPPING PIPETTE AND SPECIMEN SAMPLER TO BE USED THEREIN

CROSS REFERENCE TO RELATED APPLICATIONS

The present application is a continuation of U.S. patent application Ser. No. 13/359,841, filed Jan. 27, 2012, which is the divisional of U.S. patent application Ser. No. 12/224,753, filed Sep. 5, 2008, which is the U.S. National Phase of International Patent Application Serial No. PCT/JP2007/054650, filed Mar. 9, 2007, which, in turn, claims the benefit of Japanese Patent Application Serial No. 2006-064030, filed Mar. 9, 2006. The foregoing applications are hereby incorporated by reference in their entireties.

TECHNICAL FIELD

The present invention relates to a method for taking a sample such as blood to be collected in a vacuum blood collection tube, and a test method of the sample, while also relating to a dropping pipette and a sample collecting tool used for such purposes.

BACKGROUND ART

Tests for checking the blood components are widely performed to grasp the condition of a human body. To perform such a test, blood as a sample is drawn from a human body and collected in e.g. a vacuum blood collection tube (see e.g. Patent document 1). The blood collected in the vacuum blood collection tube is subjected to a test for hemoglobin (hereinafter referred to as "Hb") or C-reactive protein (hereinafter referred to as "CRP") by an optical technique or a test for counting white blood cells, red blood cells and blood platelets, for example.

FIG. 16 shows an example of stopper remover to be used before transferring the blood (now shown) from a vacuum blood collection tube Cn to a test apparatus. Specifically, the illustrated stopper remover X is used for pulling out the stopper St from the vacuum blood collection tube Cn, with the sample storage portion Sr held. The stopper remover X includes a rod 91 and a pair of levers 92. The rod 91 includes an end 91a, which may be made of rubber, and is vertically movable. The paired levers 92 include ends formed with pawls 92a. The levers are vertically movable and can open and close. Firstly, to pull out the stopper St, the rod 91 is moved down to press the end 91a against the stopper St. Then, the paired levers 92 are closed to bring the pawls 92a into engagement with the lower end of the stopper St. In this state, the rod 91 and the levers 92 are moved upward. As a result, the stopper St is removed from the sample storage portion Sr. Thereafter, the sample storage portion Sr is set to the test apparatus for testing the blood as the sample.

However, to improve the airtightness of the vacuum blood collection tube Cn, the stopper St is strongly pressed into the sample storage portion Sr. Thus, to pull out the stopper St, a large force is required. Thus, in reaction to the pulling force, the blood adhering to the stopper St may be scattered. Since the scattered blood can be a source of infection, the works such as properly wiping off the blood and sterilizing need to be performed. The scattering of blood may occur even when the stopper St is manually removed without using the above-described stopper remover X. In this way, the operation to pull out the stopper St from the vacuum blood collection tube has a hygiene problem.

Patent Document 1: JP-A-2005-224366
Patent Document 2: JP-A-5-228379

DISCLOSURE OF THE INVENTION

An object of the present invention, which is proposed under the circumstances described above, is to provide a method for taking a sample, a method for testing a sample, and a dropper and a sample collecting tool used for such purposes, which are capable of properly maintaining hygiene.

According to a first aspect of the present invention, there is provided a method for taking a sample comprising the steps of drawing a sample into a sample container and transferring at least part of the sample from the sample container to a sample storage space of a dropper. The sample container includes a sample storage portion and a stopper sealing the sample storage portion, and the drawing is performed by stabbing a hollow needle into the stopper. The dropper includes an internal space at least part of which is the sample storage space for storing the sample and which includes a volume changeable space defined by an elastically deformable portion having flexibility. The dropper further includes an insertion portion including a through-hole connected to the internal space, and the transfer of the sample is performed by inserting the insertion portion into a through-hole formed in the stopper by the stabbing of the hollow needle into the stopper.

According to a second aspect of the present invention, there is provided a method for testing a sample. The method comprises testing the sample stored in the sample storage space after the sample taking method as set forth in claim 1 is performed.

According to a third aspect of the present invention, there is provided a dropper comprising an internal space at least part of which is a sample storage space for storing a sample and which includes a volume changeable space defined by an elastically deformable portion having flexibility, and an insertion portion including a through-hole connected to the internal space. The insertion portion is capable of being inserted into a through-hole formed in a stopper by stabbing a hollow needle into the stopper.

In a preferred embodiment, the insertion, portion includes a portion, whose cross sectional area reduces as progressing toward the end of the insertion portion.

In a preferred embodiment, the insertion portion includes an end having a periphery comprising a curved surface.

In a preferred embodiment, the insertion portion includes an end formed with a surface inclined with respect to an axial direction of the through-hole.

In a preferred embodiment, the insertion portion includes a large-cross-section portion which is larger in cross sectional area than adjacent portions in an axial direction of the through-hole.

In a preferred embodiment, the dimension of the insertion portion in a cross section perpendicular to an axial direction of the through-hole is not more than 3 mm.

In a preferred embodiment, the insertion portion has a length of not more than 30 mm.

In a preferred embodiment, the insertion portion is made of resin.

In a preferred embodiment, the resin is polypropylene, Polystyrene-based resin or nylon-based resin.

In a preferred embodiment, the resin is a self-lubricating material such as polyacetal or polyamide (nylon 6, nylon 66, nylon 11 or nylon 12) or a material containing silicone.

According to a fourth aspect of the, present invention, there is provided a dropper comprising an internal space at least part of which is a sample storage space for storing a sample and which includes a volume changeable space defined by an elastically deformable portion having flexibility, and an insertion portion including a through-hole connected to the internal space. The dropper further includes a rigid portion defining part of the internal space, located between the insertion portion and the elastically deformable portion and formed integrally with at least the elastically deformable portion.

In a preferred embodiment, the rigid portion comprises a portion formed with a plurality of grooves extending in a direction along a central axis of the through-hole.

In a preferred embodiment, the insertion portion includes a portion whose cross sectional area reduces as progressing toward an end of the insertion portion.

In a preferred embodiment, the insertion portion includes an end having a periphery comprising a curved surface.

In a preferred embodiment, the insertion portion includes an end formed with a surface inclined with respect to an axial direction of the through-hole.

In a preferred embodiment, the insertion portion includes a large-cross-section portion which is larger in cross sectional area than adjacent portions in an axial direction of the through-hole.

In a preferred embodiment, the dimension of the insertion portion in a cross section perpendicular to an axial direction of the through-hole is not more than 3 mm.

In a preferred embodiment, the insertion portion has a length of not more than 30 mm.

In a preferred embodiment, the insertion portion is made of resin.

In a preferred embodiment, the resin is polypropylene, polystyrene-based resin or nylon-based resin.

In a preferred embodiment, the resin is a self-lubricating material such as polyacetal or polyamide (nylon 6, nylon 66, nylon 11 or nylon 12) or a material containing silicone.

According to a fifth aspect of the present invention, there is provided a sample collecting tool comprising a dropper provided according to the third or fourth aspect of the present invention and a guide which is generally cylindrical and capable of being fitted to the dropper to accommodate the insertion portion on a central axis in an internal space thereof.

Other features and advantages of the present invention will become more apparent from the detailed description given below with reference to the accompanying drawings.

BEST MODE FOR CARRYING OUT THE INVENTION

Preferred embodiments of the present invention will be described below with reference to the accompanying drawings.

Figure 1:
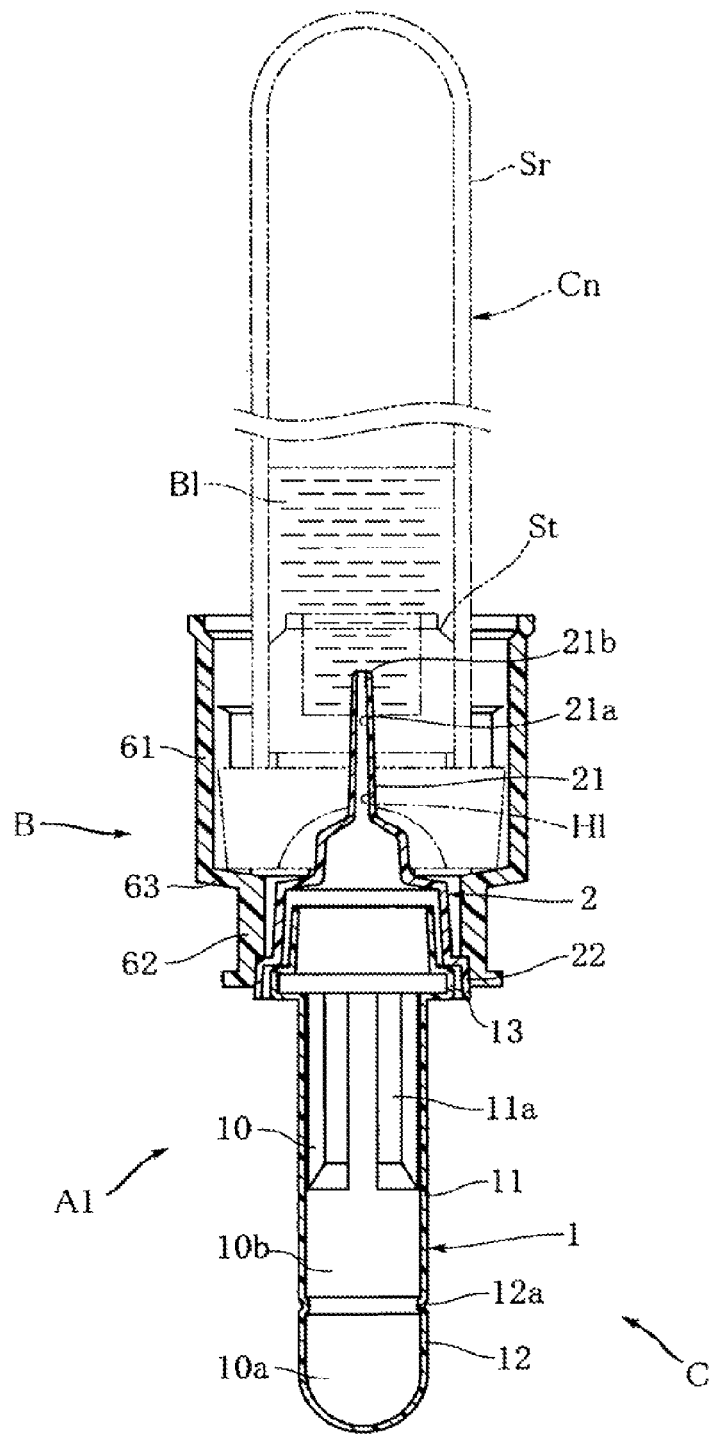
FIG. 1 is a sectional view showing a dropper and a sample collecting tool according to the present invention.
Figure 2:
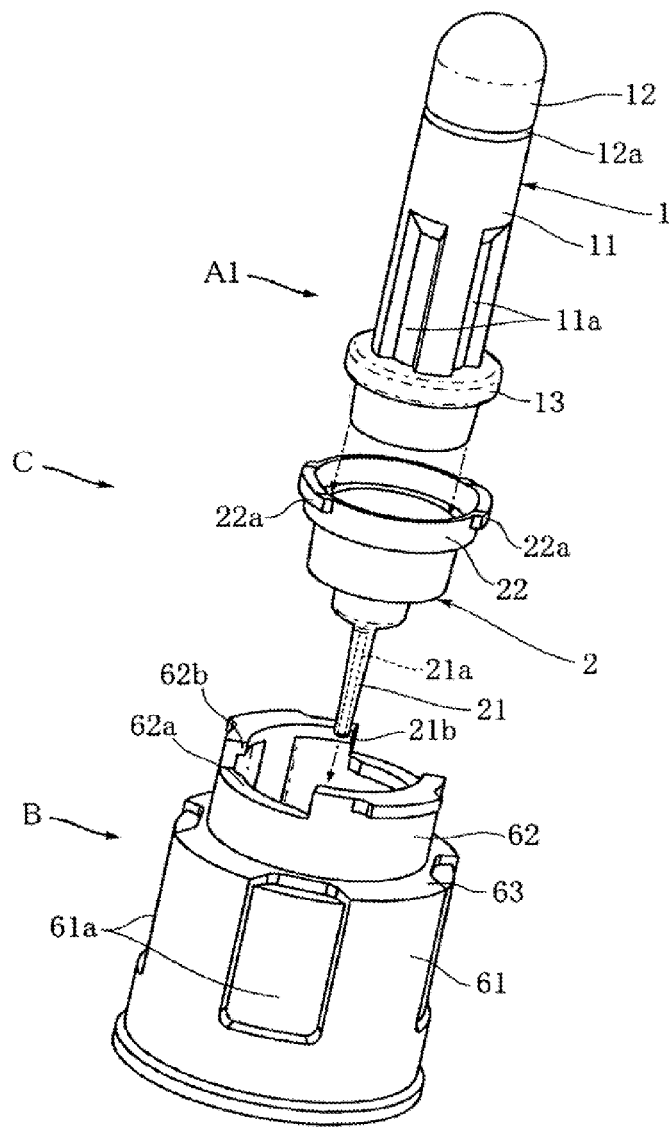
FIG. 2 is an exploded perspective view showing the dropper and the sample collecting tool according to the present invention.

FIGS. 1 and 2 show an example of sample collecting tool according to the present invention. The illustrated sample collecting tool C includes a dropper A1 and a guide B. The sample collecting tool is used for taking blood B1, which is an example of sample, from a vacuum blood collection tube Cn. The vacuum blood collection tube Cn is an example of sample container of the present Invention and includes a sample storage portion Sr and a stopper St.

The dropper A1 comprises a main body 1 and a cap 2, and includes an internal space 10. As shown in FIG. 2, the main body 1 and the cap 2 are connected to each other by screwing, fitting or bonding, for example. The dropper A1 is designed to take the blood B1 from the sample storage portion Sr without pulling out the stopper St.

Figure 3:
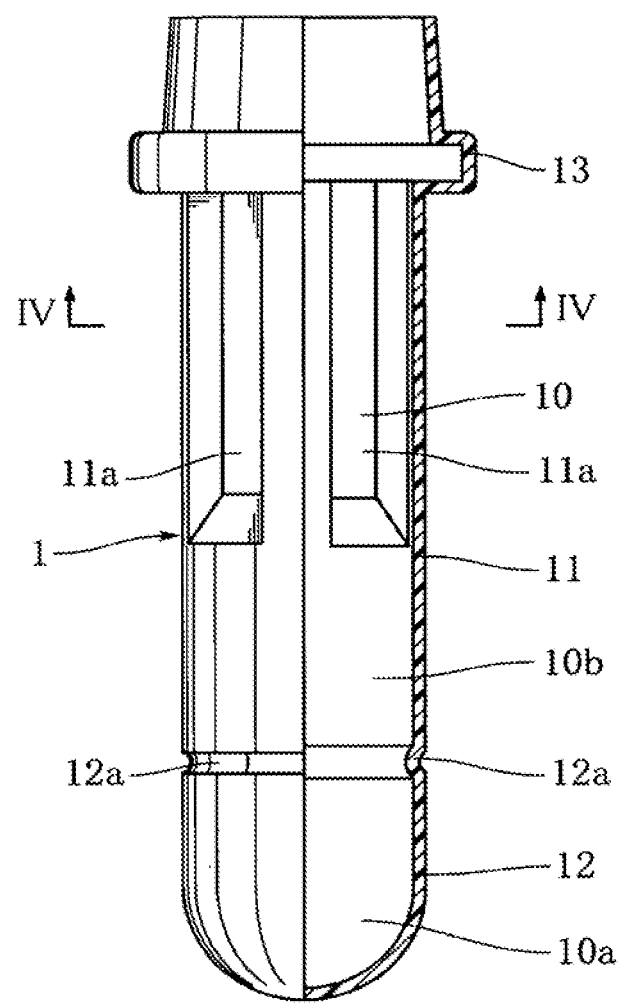
FIG. 3 is a front view, partially in section, showing the main body of the dropper according to the present invention.
Figure 4:
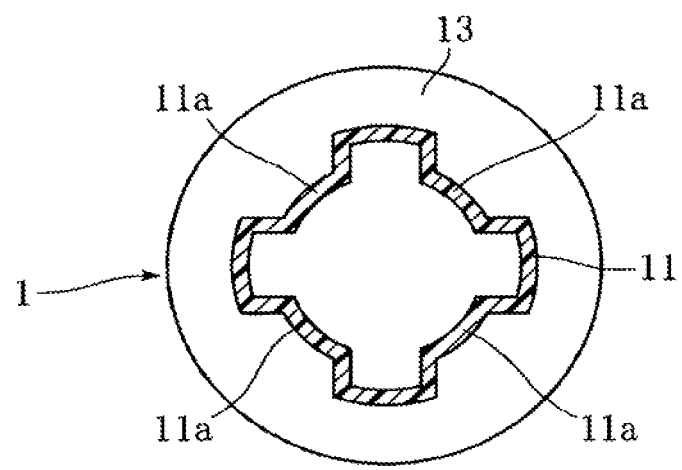
FIG. 4 is a sectional view taken along lines IV-IV in FIG. 3.

The main body 1 is made of a translucent, appropriately soft resin such as low-density polyethylene and includes a holder 11 and an elastically deformable portion 12. The holder 11 is generally cylindrical. In connecting the main body 1 and the cap 2 to each other, the holder is held. The holder 11 is an example of rigid portion of the present invention. As shown in FIGS. 3 and 4, the holder 11 is formed with a plurality of grooves 11a. The grooves 11a enhance the rigidity of the holder 11. Thus, even when e.g. a force to screw the main body 1 into the cap 2 is applied, the holder 11 is hardly deformed.

The elastically deformable portion 12 comprises a cylindrical portion connected to the holder 11 and a dome-shaped portion connected to the cylindrical portion. The elastically deformable portion 12 easily deforms elastically by such a force as that applied in pinching it with fingers, for example. The elastically deformable portion 12 defines therein a volume changeable space 10b which is part of the inner space 10. When the elastically deformable portion 12 is deformed, the volume of the volume changeable space 10b changes.

The elastically deformable portion 12 is formed with a groove 12a. The groove 12a extends around the elastically deformable portion 12 and is used as a mark for taking the blood B1 by an amount suitable for the test. In this embodiment, as shown in FIGS. 1 and 3, the portion of the inner space 10 which is lower than the groove 12a serves as a sample storage space 10a for storing a sample such as blood B1. For instance, the sample storage space 10a is capable of storing 200 to 300 μl of blood B1.

A flange 13 is formed at an end of the holder 11. The flange 13 has a diameter which is larger than that of the holder 11 and the elastically deformable port on 12 and is utilized for controlling the mounting depth of the main body 1 to the cap 2. The flange 13 is also utilized for mounting the main body 1 to a centrifugal separator after the blood sampling is performed. Specifically, a centrifugal separator of this type generally includes a port in the form of a deep hole for mounting the main body 1. By bringing the flange 13 into engagement with the edge of the port, the main body 1 is prevented from entering the port too deeply.

Figure 5:
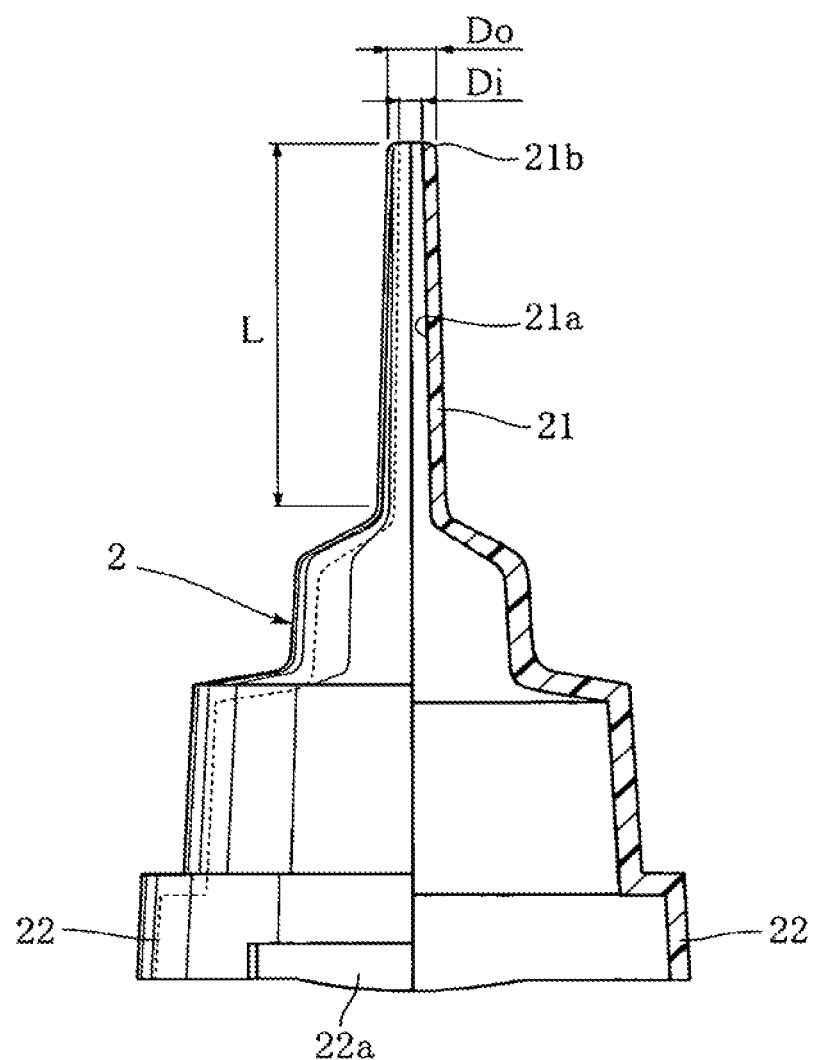
FIG. 5 is a front view, partially in section, showing the cap of the dropper according to the present invention.

The cap 2 is made of an appropriately hard resin such as polypropylene and includes an insertion portion 21 and a flange 22. The insertion portion 21 is a portion to be inserted into a hole H1 formed in the stopper St and thinner than other portions of the cap 2 and the main body 1. The insertion portion 21 is formed with a through-hole 21a. The through-hole 21a is used for transferring part of the blood B1 from the sample storage portion Sr to the inner space 10 of the main body 1. As shown in FIG. 5, the cross section of the insertion portion 21 becomes smaller as progressing toward the end. The periphery of the end of the insertion portion 21A comprises a curved surface 21b. In this embodiment, the insertion portion 21 has a length L of about 10 mm, an outer diameter Do of about 1 mm and an inner diameter Di of about 20 μm. The dimensions of the insertion portion are not limited to these values, but it is preferable that the length L is not more than 30 mm, the outer diameter Do is not more than 3 mm; and the inner diameter Di is not less than 10 μm.

The flange 22 is provided at the end of the cap 2 which is opposite from the insertion portion 21. The flange 22 is used for fitting the cap 2 to the guide B. As shown in FIGS. 2 and 5, the flange 22 is formed with two projections 22a. The two projections 22a are brought into engagement with part of the guide B.

Figure 6:
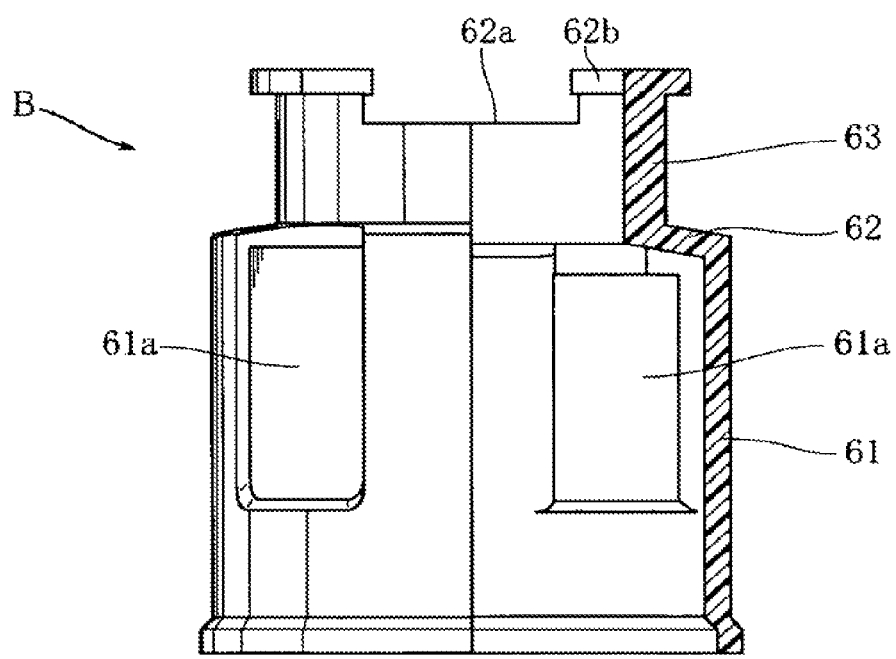
FIG. 6 is a front view, partially in section, showing the guide of a sample collecting tool according to the present invention.

The guide B is used for arranging the dropper A1 generally coaxially with the vacuum blood collection tube Cn. The guide includes two cylindrical portions 61 and 62; and a stepped portion 63 connecting the two cylindrical portions 61 and 62 to each other. As shown in FIG. 1, the cylindrical portion 61 serves to accommodate the stopper St of the vacuum blood collection tube Cn. As shown in FIG. 6, the cylindrical portion 61 is formed with a plurality of recesses 61a. The recesses 61a enhance the rigidity of the cylindrical portion 61 The lower end of each recess 61a can be utilized for controlling the mounting depth of a vacuum blood collection tube having a shape which is different from that of the vacuum blood collection tube Cn shown in FIG. 1. The stepped portion 63 is to engage the stopper St to control the mounting depth of the vacuum blood collection tube Cn. The guide B is made of an appropriately hard resin such as polypropylene, polystyrene-based resin or nylon-based resin. By the use of these materials, the guide B has such a high rigidity that it hardly deforms due to the force, applied in mounting the dropper A1 or the vacuum blood collection tube Cn. Instead of the cylindrical portion 61 of this embodiment, the guide B may include a plurality of legs extending from the cylindrical portion 62. Preferably, the legs are arranged to flare from the cylindrical portion 62, i.e., the distance between adjacent legs increases as separating from the cylindrical portion 62. With this arrangement, various kinds of vacuum blood collection tubes Cn having different sizes can be mounted properly.

The cylindrical portion 62 is a portion to which the dropper A1 is mounted. The cylindrical portion 62 is smaller in diameter than the cylindrical portion 61. As shown in FIG. 2, the cylindrical portion 62 is formed with two cutouts 62a and two eaves 62b. The two cutouts 62a are formed at an end of the cylindrical portion 62 to be arranged across the central axis of the cylindrical portion 62 and generally rectangular. Each of, the two eaves 62b is provided between the two cutouts 62a and extends from the edge of the cylindrical portion 62 toward the central axis of the cylindrical portion 62.

To mount the dropper Al to the guide B, with the two projections 22a of the dropper A1 aligned with the two cutouts 62a of the guide B, the insertion portion 21 of the dropper A1 is put into the guide B. Then, after the two projections 22a are received in the two cutouts 62a, respectively, the dropper A1 is rotated around the central axis relative to the guide B. As a result, the two projections 22a of the dropper A1 engage the two eaves 62b of the guide B. Thus, the dropper A1 is mounted to the guide B. As shown in FIG. 1, by this mounting, the flange 22 of the dropper A1 is fitted to the inner surface of the cylindrical portion 62 of the guide B. Thus, the insertion portion 21 is arranged coaxially with the cylindrical portions 61, 62.

A method for testing a sample according to the present invention will be described below.

Figure 7:
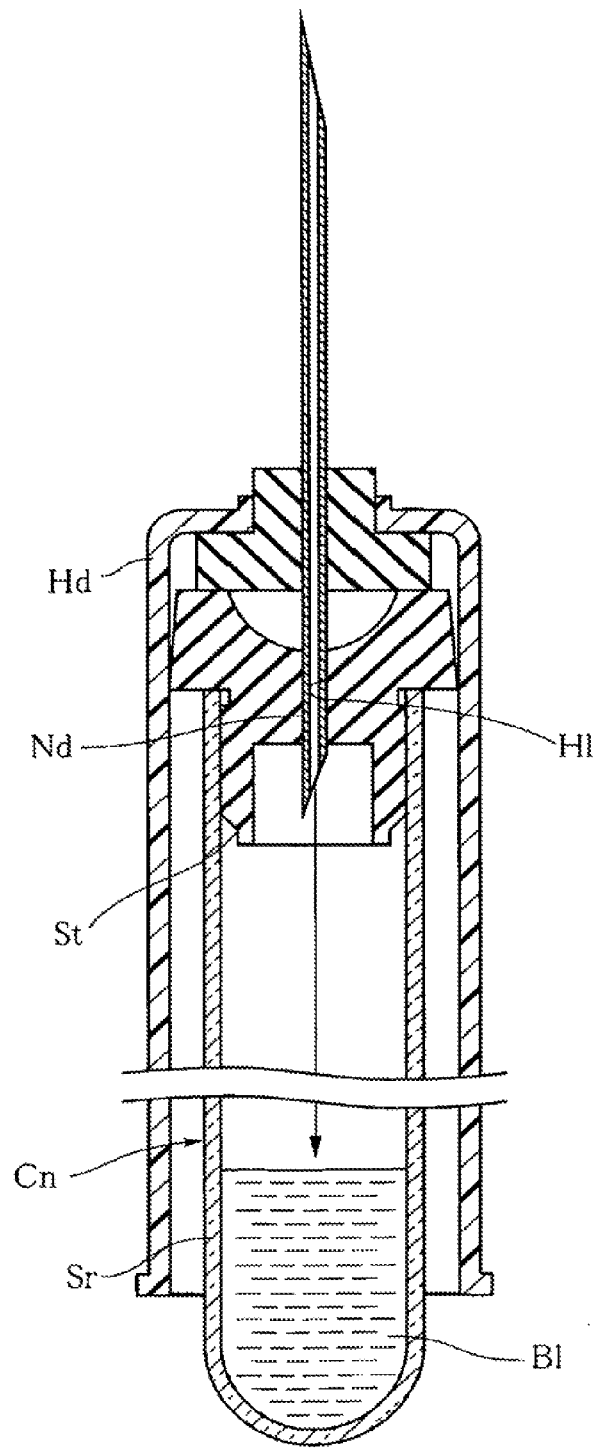
FIG. 7 is a sectional view showing the step of drawing blood into a vacuum blood collection tube in a method for testing a sample according to the present invention.

FIG. 7 shows the step of drawing blood B1 into the sample storage portion Sr of a vacuum blood collection tube Cn. First, a vacuum blood collection tube Co kept at a room temperature and a blood collection holder Hd including a needle Nd are prepared. A tourniquet (not shown) is put around an arm (not shown) of a patient whose blood B1 is to be tested. Then, an upper portion of the needle Nd is stabbed into the arm. In this state, the blood collection holder Hd is fixed. Then, the vacuum blood collection tube Cn is inserted into the blood collection holder Hd. By this insertion, the lower portion of the needle Nd is stabbed into the substantial center of the stopper St. As a result, blood B1 starts to flow from the arm of the patient into the sample storage portion Sr of the vacuum blood collection tube Co. When a predetermined amount of blood B1 is collected in the sample storage portion Sr, the vacuum blood collection tube Co is pulled out from the blood collection holder lid. By the above-described stabbing of the needle Nd, a hole H1 is formed in the stopper St. However, since the stopper St is generally made of rubber and pressed into the sample storage portion Sr, the hole H1 immediately closes when the needle Nd is pulled out.

Figure 8:
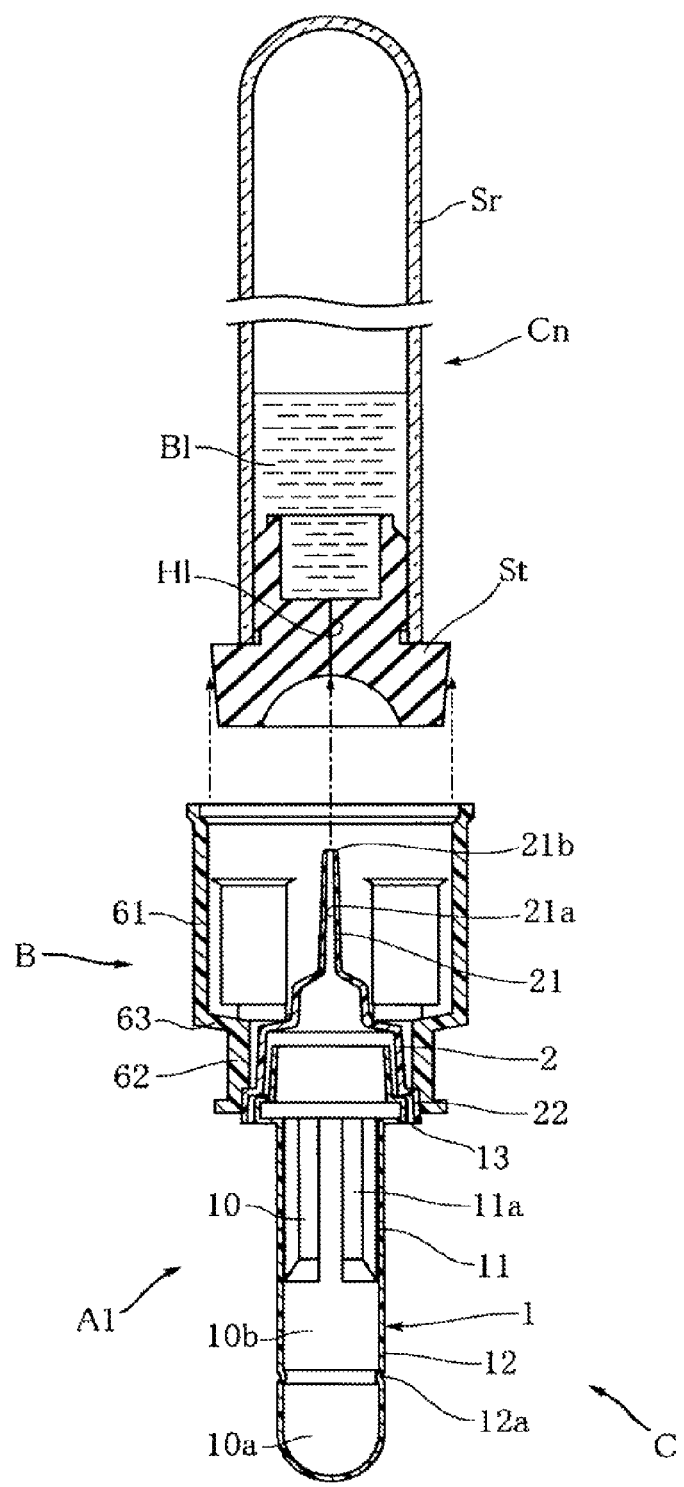
FIG. 8 is a sectional view showing the step of mounting a sample collecting tool to a vacuum blood collection tube in the method for testing a sample according to the present invention.

Then, as shown in FIG. 8, the sample collecting tool C is mounted to the vacuum blood collection tube Cn. Specifically, for instance, the mounting is performed by turning the vacuum blood collection tube Cn upside down from the state shown in FIG. 7 and inserting the stopper St into the cylindrical portion 61 of the holder B. When the end of the stopper St enters the cylindrical portion 61, the cylindrical portion 61 and the stopper St are coaxial with each other. Thus, the insertion portion 21 of the dropper A1 is positioned directly under the hole H1 of the stopper St. When the vacuum blood collection tube Cn is further moved downward, the insertion portion 21 enters the hole H1 while spreading the hole H1. The stopper St is inserted until it engages the stepped portion 63, so that the insertion portion 21 penetrates the stopper St, as shown in FIG. 1.

Figure 9:
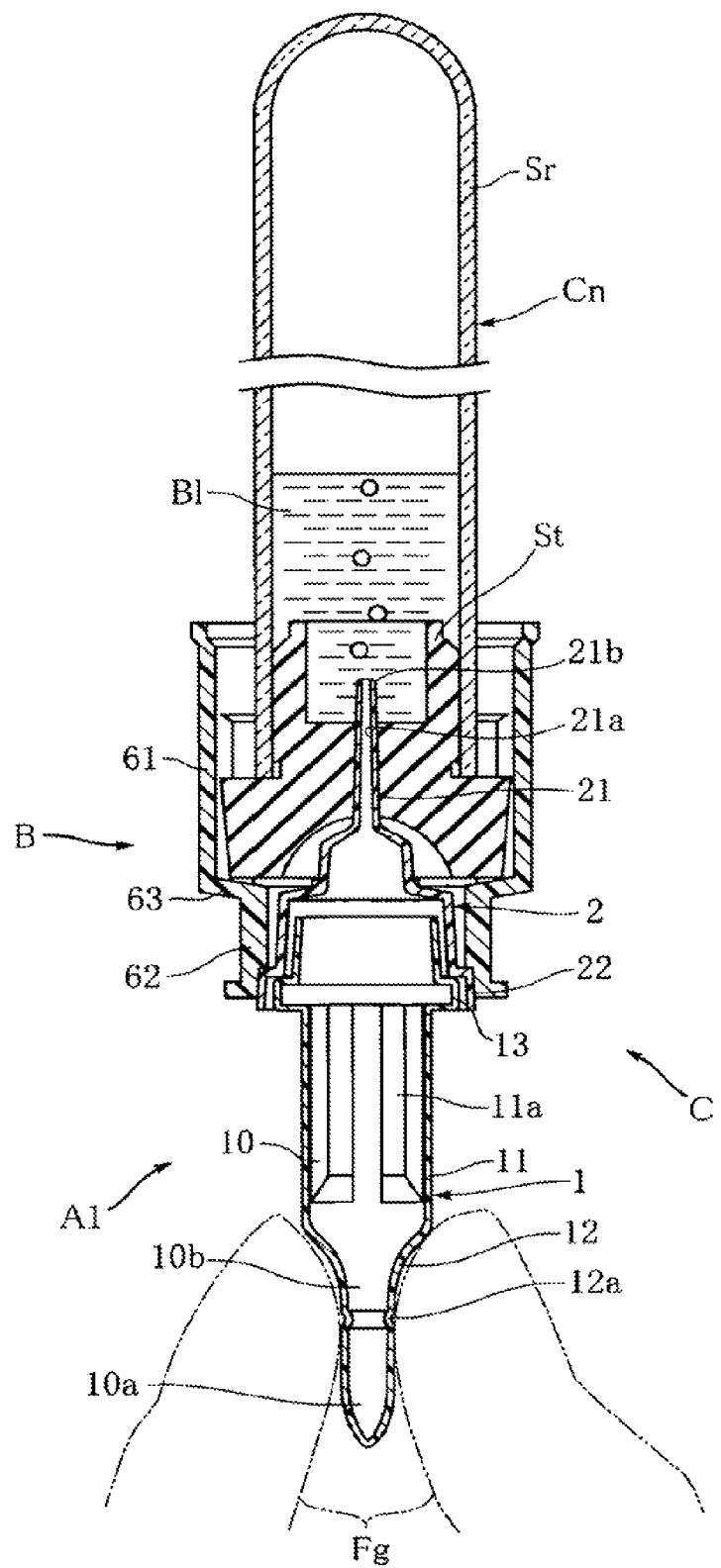
FIG. 9 is a sectional view showing the step of pressing the elastically deformable portion in the method for testing a sample according to the present invention.

Then, as shown in FIG. 9, the elastically deformable portion 12 of the dropper A1 is pressed with fingers Fg. Since the elastically deformable portion 12 is made of low-density polyethylene which is an appropriately soft resin, it can be easily pressed manually. By pressing the elastically deformable portion 12, the volume of the volume changeable space 10b reduces, and the air corresponding to the decrement of the volume is released into the vacuum blood collection tube Cn.

Figure 10:
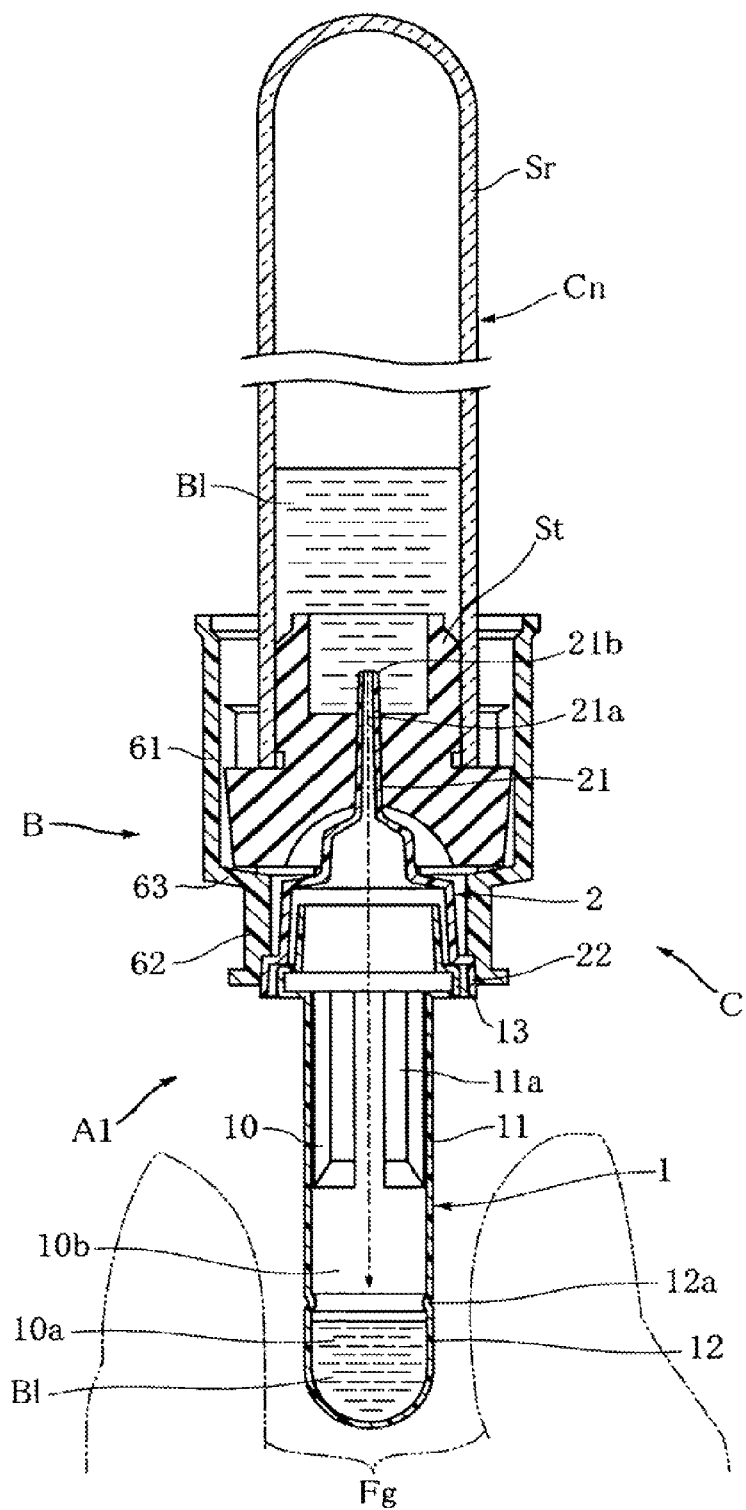
FIG. 10 is a sectional view showing the step of taking the blood in the method for testing a sample according to the present invention.

Then, as shown in FIG. 10, the fingers Fg are opened to release the elastically deformable portion 12. When the force applied by the fingers Fg is removed, the elastically deformable portion 12 returns to its original shape, so that the volume of the volume changeable space 10b increases. As a result, the pressure in the internal space 10 becomes lower than that in the sample storage portion Sr. Thus, part of the blood 91 stored in the sample storage portion S4 is transferred into the internal space 10 of the dropper A1 through the insertion portion 21. This transfer of the blood B1 is continued until the blood fills the sample storage space 10a to reach the groove 12a. In this way, the blood B1 of the amount necessary for the test is taken from the vacuum blood collection tube Cn into the dropper A1.

Thereafter, the vacuum blood collection tube Cn is pulled out from the sample collecting tool C. The dropper A1 may be removed from the guide B as required. Then, the blood B1 is transferred from the dropper A1 into a test apparatus (not shown). In the test apparatus, a test for Hb or CRP by an optical technique, a test for counting white blood cells, red blood cells and blood platelets and so on may be performed.

The advantages of the dropper A1, the sample collecting tool C and the method for testing a sample using these will be described below.

According to this embodiment, the blood B1 is taken from the vacuum blood collection tube Cn by inserting the insertion portion 21 of the dropper A1 into the hole H1 formed in the stopper St. Thus, it is possible to take the blood B1 without pulling out the stopper St from the vacuum blood collection tube Cn. Thus, there is no possibility that the blood B1 scatters, which may occur in pulling out the stopper St. Thus, the place where the work of taking blood B1 from the vacuum blood collection tube Cn is performed and the test apparatus for testing the blood B1 are kept hygienic.

Unlike the permanent part of an apparatus designed to automatically take blood B1 from the vacuum blood collection tube On, the dropper A1 used for taking the blood B1 from the vacuum blood collection tube Cn has a manually-operable, simple structure. Further, a common resin such as polyethylene or polypropylene is employed as the material. Thus, the dropper A1 can be manufactured at a relatively low cost, so that the dropper A1 is suitable for use as a disposable part. The use of a disposable dropper is convenient, because cleaning or sterilization is not necessary. Further, the use of a disposable dropper is advantageous for keeping the place where the work of taking blood B1 from the vacuum blood collection tube Cn is performed and the test apparatus to test the blood B1 hygienic.

The end of the insertion portion 21 of the dropper A1 is formed with the curved surface 21b. Thus, when the insertion portion 21 is pressed against the hole H1 of the stopper St, the end of the insertion portion 21 is not caught on the edge of the hole H1. Thus, the insertion portion 21 smoothly enters the hole H1. Further, since the cross section of the insertion portion 21 is smaller at a port ion closer to the end, the insertion portion 21 spreads the hole H1 in entering the hole H1. Thus, the insertion portion 21, which is relatively thin and long, is inserted into the hole H1 continuously and smoothly.

The insertion portion 21 is made of polypropylene and hence appropriately hard. Thus, the insertion portion 21 is unlikely to break in entering the hole H1 of the stopper St, which is generally made of rubber. To set the outer diameter of the insertion portion 21 to not more than 3 mm is particularly suitable for achieving both the smooth insertion and the prevention of breakage of the insertion portion 21. Further, when the length of the insertion portion 21 is not more than 30 mm, the insertion portion 21 is prevented from buckling due to the manual insertion. Moreover, since the end of the insertion portion 21 is formed with the curved surface 21b and the cap 2 is made of polypropylene which is a resin, the end of the insertion portion 21 does not hurt the body of the user of the dropper A1 or sample collecting tool C. The material of the insertion portion 21 is not limited to polypropylene and may be other materials as long as they are suitable for the insertion into the hole H1 of the stopper St, which may be made of rubber. For instance, polystyrene-based resin or nylon-based resin may be employed. With the use of these materials, an appropriately hard insertion portion 21 is obtained. Alternatively, the insertion portion 21 maybe made of a self-lubricating material (e.g. polyacetal or polyamide (e.g. nylon 6, nylon 66, nylon 11 or nylon 12)) or a material containing silicone. With the use of these materials, the lubricity for the stopper St enhances. The insertion portion 21 may be subjected to surface modification by e.g. coating, heat treatment or infrared irradiation.

By employing the structure made up of two parts, i.e., the main body 1 and cap 2, the dropper A1 including the hard insertion portion 21 and the soft elastically deformable portion 12 is obtained. With this arrangement, the insertion portion 21 is smoothly inserted into the hole H1 of the stopper St, while the extent to which the elastically deformable portion 12 is pressed with fingers Fg is easily adjusted. The same advantages may be obtained by forming the dropper A1 as a single-piece part by using e.g. resin. In this case, the portion corresponding to the insertion portion 21 is made to have an appropriately large wall thickness, while the portion corresponding to the elastically deformable portion 12 is made to have a relatively small wall thickness.

Polypropylene for forming the insertion portion 21 has an appropriately high hydrophobicity and water repellency. Thus, the sample such as blood B1 applied to the insertion portion 21 is easily repelled, which is suitable for preventing the sample from scattering or dripping.

In the sample collecting tool C, by mounting the dropper A1 to the guide B, the insertion portion 21 of the dropper A1 is reliably positioned coaxially with the hole H1 of the stopper St. Thus, the insertion portion 21 is inserted into the hole H1 without the need for visually aligning the insertion portion 21 with the hole H1. Moreover, the stopper St moves along the inner surface of the cylindrical portion 61 of the guide B. Thus, the insertion portion 21 and the hole H1 do not incline largely with respect to each other.

The holder 11 has an appropriately high rigidity owing to the provision of the grooves 11a. Thus, the holder 11 is not deformed due to the force applied in connecting the main body 1 and the cap 2 to each other or the force applied in pressing the elastically deformable portion 12. Further, by forming the grooves in a limited region, both of the holder 11 which has an appropriately high rigidity and the elastically deformable portion 12 which is flexible are obtained while making the main body 1 as a single-piece part. This is advantageous for reducing the number of parts for forming the dropper A1.

Before the blood B1 is taken, a separating agent for separating the blood B1 into blood plasma and blood cell components may be put in the main body 1 in advance. When the blood B1 mixed with the separating agent in the internal space 10 is centrifuged, the blood is separated into blood cell components, the separating agent and blood plasma in the mentioned order from the sample storage space 10*a* toward the volume changeable space 10*b*. In this state, when the elastically deformable portion 12 is pinched with fingers, blood plasma, the separating agent and blood cell components move in the mentioned order toward the insertion portion 21. The portion of the internal space 10 which is formed with grooves ha is smaller in cross section than the elastically deformable portion 10*a*. Thus, when, the separating- agent reaches the portion formed with the grooves 11*a*, the dimension of the separating agent in the direction along the central axis of the main body 1 increases. This prevents the blood cell components from passing over the separating agent to mix with the blood plasma within the internal space 10. When the separating agent contains a coagulant, the blood B1 is separated into blood serum and protein which is a clotting factor. In this case again, the protein is prevented from passing over the separating agent to mix with the blood serum.

Alternatively, glass fiber may be put in the main body 1 in advance. Glass fiber is likely to adsorb red blood cells contained in blood. Thus, in discharging blood from the main body 1 for testing, the discharge of red blood cells is prevented. Generally, in a biochemical test, an error is likely to occur when the sample tested contains a large amount of red blood cells like that having a high hematocrit. The use of glass fiber reduces the influence of red blood cells, whereby the accuracy of the test is enhanced.

FIGS. 11-15 show other embodiments of the present invention. In these figures, the elements which are identical or similar to those of the foregoing embodiment are designated by the same reference signs as those used for the foregoing embodiment.

Figure 11:
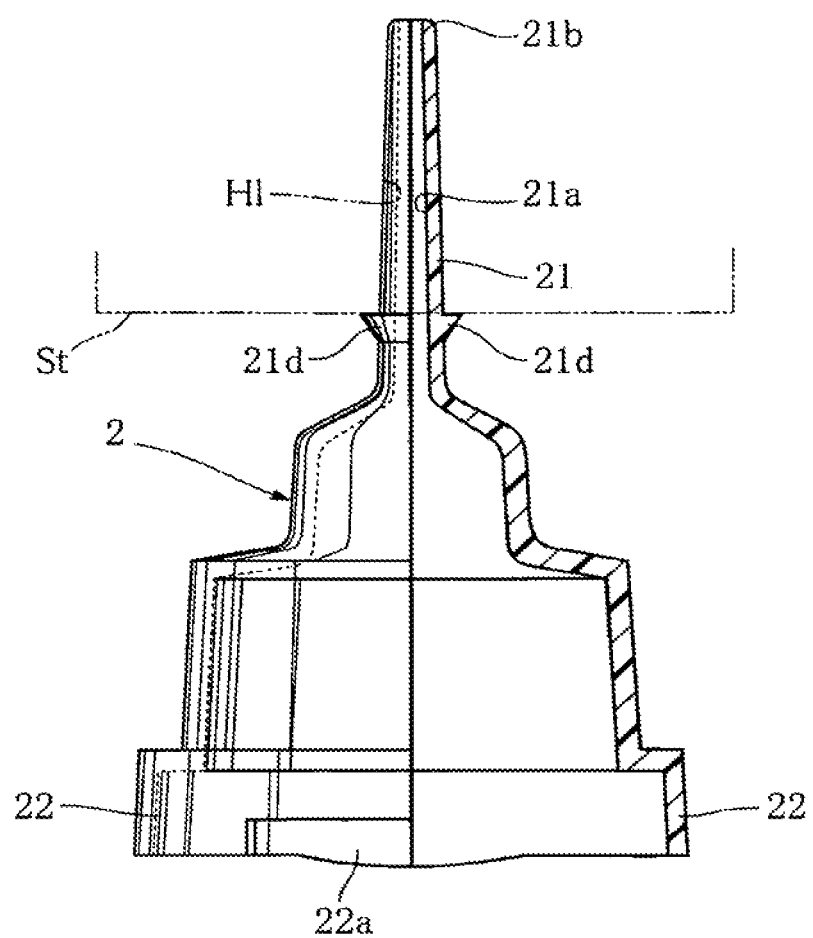
FIG. 11 is a front view, partially in section, showing the cap of another example of dropper according to the present invention.

FIG. 11 shows another example of insertion portion 21 of the dropper Al. Unlike the foregoing embodiment, the insertion portion 21 shown in the figure includes a large-cross-section portion 21*d*. The large-Cross-section portion 21*d* has a cross sectional area which is larger than the adjacent portions in the direction along the central axis of the through-hole 21*a*, i.e., the longitudinal direction of the insertion portion 21. In this embodiment, the end surface of the large-cross-section portion 21*d* which is closer to the end of the insertion portion 21 extends perpendicularly to the longitudinal direction of the insertion portion 21. The cross sectional area of the large-cross-section portion 21*d* increases as progressing toward the end of the Insertion portion 21.

According to this embodiment, in inserting the insertion potion 21 into the hole H1 of the stopper St, the end surface of the large-cross-section portion 21*d* engages the stopper St to produce a high resistance. Due to the resistance, the insertion portion 21 is prevented from entering too deeply into the hole H1. The cross sectional area of the large-cross-section portion 21*d* which increases as progressing toward the end of the insertion portion 21 is suitable for producing a high resistance. With this structure, the excessive insertion of the insertion portion 21 is effectively prevented not only in taking the blood B1 using the sample collecting tool C but also in taking the blood B1 using only the dropper A1.

Figure 12:
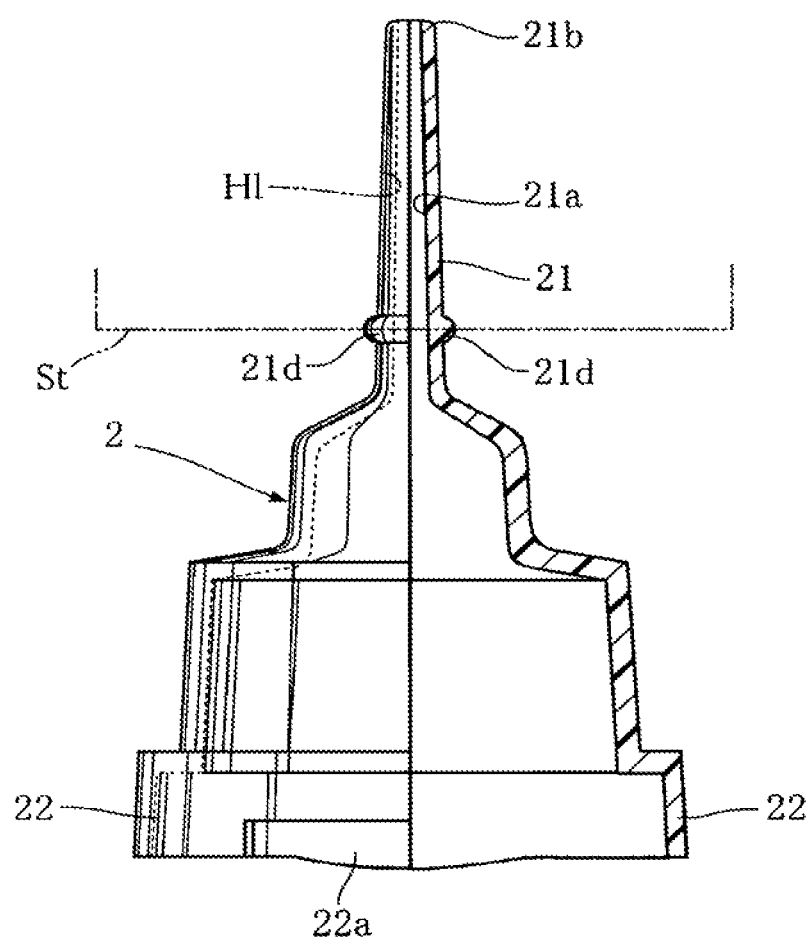
FIG. 12 is a front view, partially in section, showing the cap of another example of dropper according to the present invention.

FIG. 12 shows another example of insertion portion 21. The insertion portion 21 shown in the figure includes a large-cross-section portion 21*d* which is different from that shown in FIG. 11. Specifically, the large-cross-section portion 21*d* of this embodiment has an annular shape which is semicircular in cross section. In visually checking the insertion depth of the insertion portion 21, the large-cross-section portion hav- ing this structure is utilized as a mark indicating the proper insertion depth of the insertion portion 21. Further, when the large-cross-section port ion 21*d* is inserted into the hole H1, the hole H1 and the large-cross-section portion 21 come into contact with each other at a high pressure. Thus, an undesirable gap is not formed between the hole H1 and the insertion portion 21, so that the blood 31 is prevented from leaking.

Figure 13:
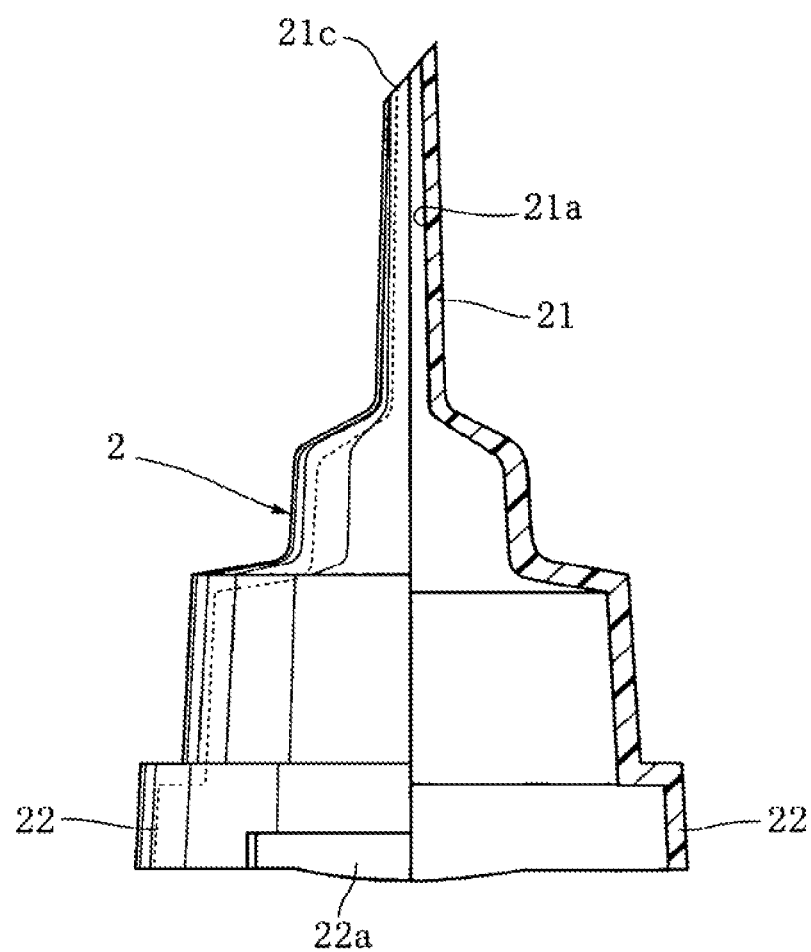
FIG. 13 is a front view, partially in section, showing the cap of another example of dropper according to the present invention.

FIG. 13 shows still another example of insertion portion 21. Unlike the foregoing embodiments, the end of the insertion portion 21 shown in the figure is formed with an inclined surface 21*c*. The surface 21*c* is inclined with respect to the longitudinal direction of the insertion portion 21. This structure ensures the smooth insertion of the insert ion portion 21 into the hole H1 of the stopper St.

Figure 14:
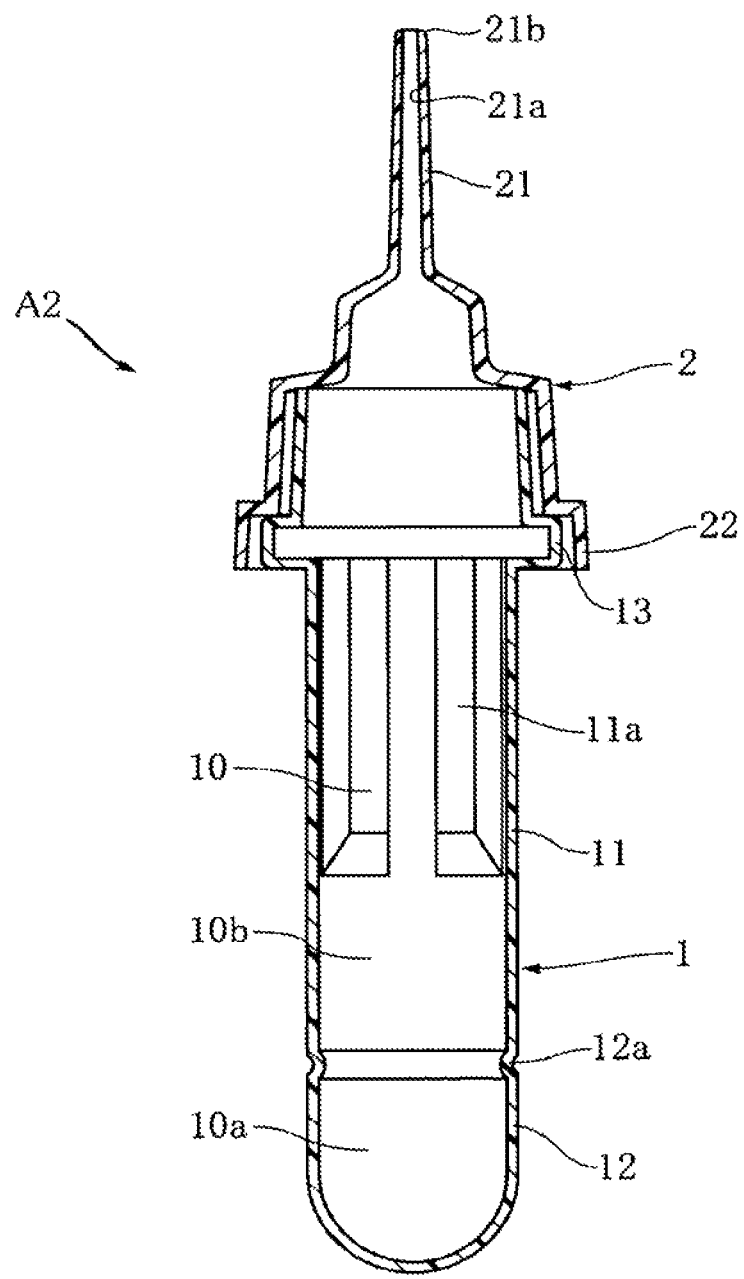
FIG. 14 is a sectional view showing another example of dropper according to the present invention.

FIG. 14 shows another example of dropper according to the present invention. The dropper A2 of this embodiment differs from the foregoing embodiment in the manner in which the main body 1 and the cap 2 come into contact with each other. Specifically, in this example, the portion of the main body 1 which extends from the flange 13 to the end thereof is longer than that of the foregoing embodiment. With this structure, the end of the main body 1 is held in contact with the inner surface of the cap 2. Thus, the main body 1 is held in contact with the cap 2 at two points, i.e., at the end and the flange 13. By increasing the contact point between the main body 1 and cap 2 in this way, the airtightness of the dropper A2 is reliably maintained. This is suitable for preventing blood from scattering and hence preventing infection.

Figure 15:
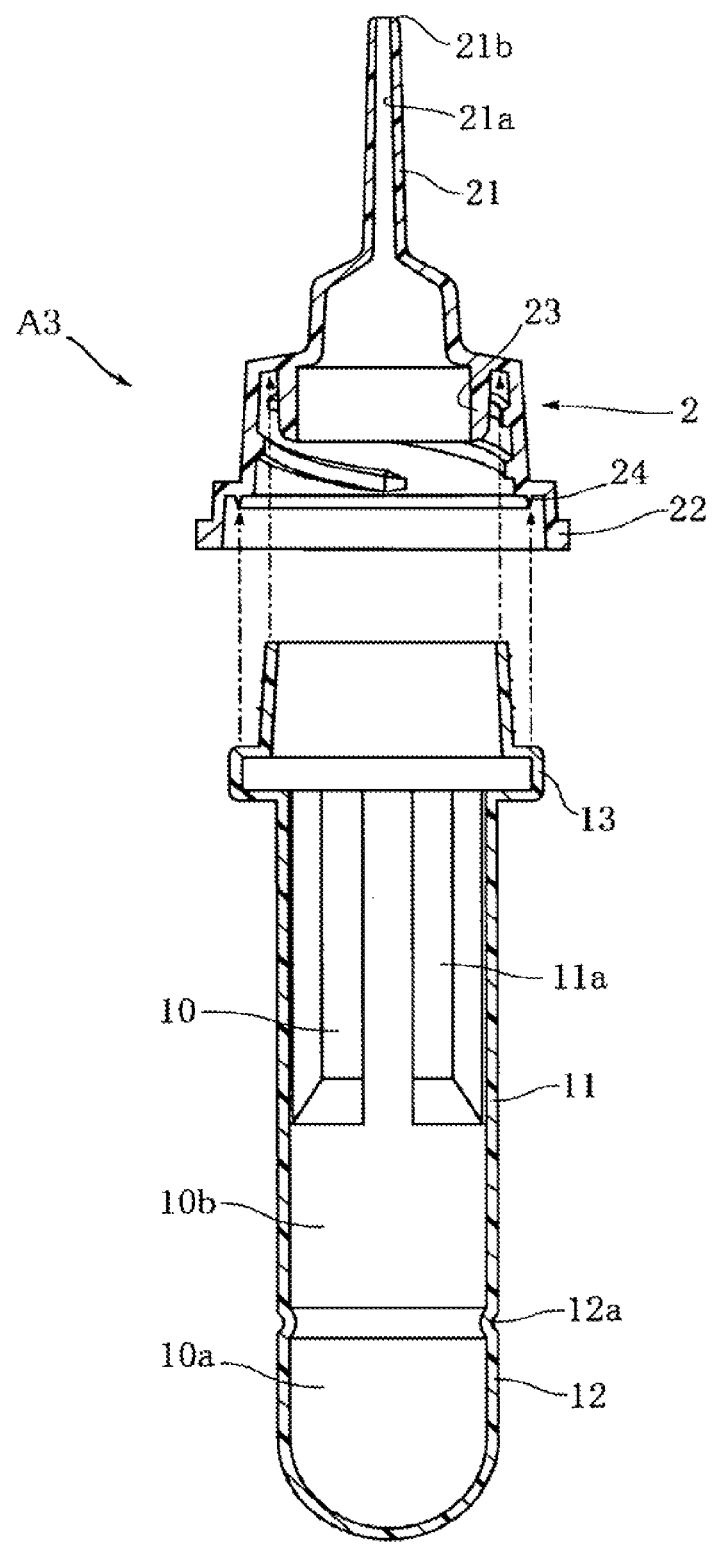
FIG. 15 is a sectional view showing another example of dropper according to the present invention.
Figure 16:
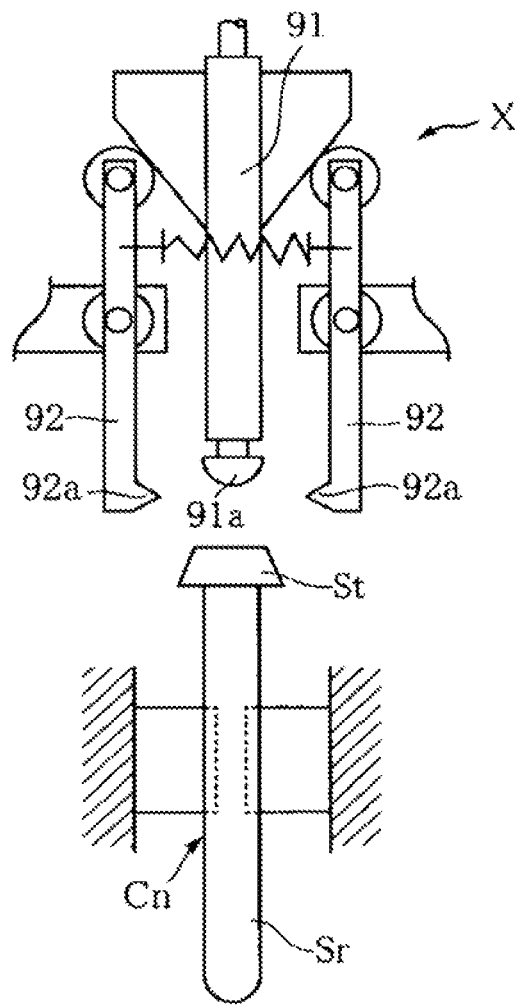
FIG. 16 is a schematic view showing a stopper remover used for a conventional method for testing a sample.

FIG. 15 shows still another example of dropper according to the present invention. The dropper A3 of this embodiment differs from the foregoing embodiments in structure of the cap 2. Specifically, the cap 2 of this embodiment is formed with an inner rib 23. The inner rib 23 has a cylindrical shape extending from the insertion portion 21 side toward the flange 22. A gap for receiving the end of the main body 1 is defined between the inner rib 23 and the outer cylindrical portion of the cap. By fitting the end of the main body 1,into the gap, the end of the main body 1 and the inner rib 23 or the outer cylindrical portion of the cap 2 come into pressure contact with each other. Thus, the airtightness of the dropper A3 is enhanced. The dropper 2 is further formed with an annular projection 24. The annular projection 24 is arranged to face the flange 13. Thus, when the main body 1 is fitted into the cap 2, the flange 13 crushes the annular projection 24. The crushed annular projection 24 functions as a sealing member. This also enhances the airtightness of the dropper A3.

The sample test method, the dropper and the sample collecting tool according to the present invention are not limited to the foregoing embodiments. The specific structure of each part of the sample test method, the dropper and the sample collecting tool may be varied in design in many ways.

The dropper according to the present invention is not limited to that made up of a main body and a cap. For instance, the dropper may have a single-piece structure. Alternatively, the holder and the elastically deformable portion of the above-described main body may be separate parts. In the foregoing embodiments, the sample storage space is included in the volume changeable space. However, the present invention is not limited to this, and the sample storage space and the volume changeable space are provided individually via e.g. a contracted portion. Although it is preferable that the dropper is made of resin, the present invention is not limited to this. The sample container of the present invention is not limited to a vacuum blood collection tube but refers to various containers for storing sample such as blood. The rigid portion of the present invention is not limited to one obtained by forming a plurality of grooves, and it is only necessary that the rigid portion has a rigidity higher than that of the elastically deformable portion. For instance, the rigid portion having such a high rigidity may be obtained by appropriately selecting the thickness or material.

The sample, test method according to the present invention is not limited to one that uses a sample collecting tool made up of a dropper and a guide. For instance, in a sample test method of the present invention, sample may be taken from a sample container such as a vacuum blood collection tube using only a dropper. The sample in the present invention is not limited to blood but includes various liquids as a target of various kinds of tests.

The invention claimed is:

1. A sample collecting tool comprising a dropper and a guide,
   wherein the dropper comprises:
   a main body with a closed end and an open end opposite to the closed end, the main body defining an internal space at least part of which is a sample storage space located at the closed end of the main body for storing a sample and which includes a volume changeable space located at the closed end of the main body and defined by an elastically deformable portion having flexibility,
   an insertion portion connected to the open end of the main body, said insertion portion having a through-hole communicating with the internal space, and
   a flange portion, said portion being located towards the open end of the main body of the dropper and said main body of the dropper extending from the flange portion towards the closed end of the dropper; and
   wherein the guide is comprised of hard resin and shaped to have a diametrically larger cylindrical portion, a stepped portion, and a diametrically smaller cylindrical portion, wherein the stepped portion is located between the diametrically larger cylindrical portion and the diametrically smaller cylindrical portion, and the diametrically larger cylindrical portion and the diametrically smaller cylindrical portion provide an outer profile of the guide, the flange portion of the dropper being fitted into the diametrically smaller cylindrical section.

2. The sample collecting tool according to claim 1, wherein the insertion portion includes a portion whose cross sectional area reduces as progressing toward an end of the insertion portion.

3. The sample collecting tool according to claim 1, wherein the insertion portion includes an end having a periphery comprising a curved surface.

4. The sample collecting tool according to claim 1, wherein the insertion portion includes an end formed with a surface inclined with respect to an axial direction of the through-hole.

5. The sample collecting tool according to claim 1, wherein the insertion portion includes a large-cross-section portion which is larger in cross sectional area than adjacent portions in an axial direction of the through-hole.

6. The sample collecting tool according to claim 1, wherein the dropper further includes a rigid portion defining part of the internal space, located between the insertion portion and the elastically deformable portion and formed integrally with at least the elastically deformable portion.

7. The dropper according to claim 6, wherein the rigid portion comprises a portion formed with a plurality of grooves extending in a direction along a central axis of the through-hole.

8. A sample collecting tool comprising a sample container, a dropper and a guide;
   wherein the sample container comprises a first sample storage space and a stopper sealing the first sample storage space, the stopper being stabbed with a hollow needle for introducing a sample into the first sample storage;
   wherein the dropper is comprised of an internal space at least part of which is a second sample storage space for storing at least part of the sample from the sample container and which includes a volume changeable space defined by an elastically deformable portion, the dropper further comprising an insertion portion and a flange at an end opposite to the insertion portion, the insertion portion including a through-hole communicating with the internal space, said at least part of the sample being transferred from the first sample storage space of the sample container to the second sample storage space by inserting the insertion portion into a through-hole formed in the stopper by the stabbing of the hollow needle into the stopper; and
   wherein the guide is comprised of hard resin and shaped to have a first cylindrical diametrically larger portion and a second cylindrical diametrically smaller portion a stepped portion in between the first and second cylindrical portion, and the first cylindrical portion and the second cylindrical portion provide an outer profile of the guide, the stopper being fitted into the first cylindrical portion in engagement with the stepped portion, the flange of the dropper being fitted into the diametrically smaller second cylindrical portion.

9. The sample collecting tool according to claim 8, wherein the insertion portion includes a portion whose cross sectional area reduces as progressing toward an end of the insertion portion.

10. The sample collecting tool according to claim 8, wherein the insertion portion includes an end having a periphery comprising a curved surface.

11. The sample collecting tool according to claim 8, wherein the insertion portion includes an end formed with a surface inclined with respect to an axial direction of the first through-hole.

12. The sample collecting tool according to claim 8, wherein the insertion portion includes a large-cross-section portion which is larger in cross sectional area than adjacent portions in an axial direction of the first through-hole.

13. The sample collecting tool according to claim 8, wherein the dropper further includes a rigid portion defining part of the internal space, located between the insertion portion and the elastically deformable portion and formed integrally with at least the elastically deformable portion.

14. The dropper according to claim 13, wherein the rigid portion comprises a portion formed with a plurality of grooves extending in a direction along a central axis of the first through-hole.

* * * * *